United States Patent [19]

Häusler et al.

[11] Patent Number: 5,922,347
[45] Date of Patent: Jul. 13, 1999

[54] PHARMACEUTICAL CHEWING GUM CONTAINING ACETYLSALICYLIC ACID

[75] Inventors: Franz Häusler, Bergish Gladbach; Joachim Maasz, Leichlingen; Thomas Valéri, Dormagen, all of Germany

[73] Assignee: Bayer Aktiengesellschaft, Leverkusen, Germany

[21] Appl. No.: 08/011,074

[22] Filed: Jan. 29, 1993

Related U.S. Application Data

[63] Continuation of application No. 07/824,425, Jan. 23, 1992, abandoned.

[30] Foreign Application Priority Data

Jan. 30, 1991 [DE] Germany ............................ 41 02 629

[51] Int. Cl.$^6$ ...................................................... A61K 9/28
[52] U.S. Cl. ............................ 424/441; 424/439; 424/440
[58] Field of Search ..................................... 424/441, 440, 424/439

[56] References Cited

U.S. PATENT DOCUMENTS

| | | | |
|---|---|---|---|
| 1,630,763 | 5/1927 | Raymer | 424/440 |
| 2,262,087 | 11/1941 | Bartlett | 424/440 |
| 2,465,233 | 3/1949 | King et al. | 167/82 |
| 2,922,747 | 1/1960 | Scanlan | 424/440 |
| 4,339,428 | 7/1982 | Tencza | 424/21 |
| 4,741,905 | 5/1988 | Huzinec | 426/3 |
| 4,753,805 | 6/1988 | Cherukuri et al. | 426/5 |
| 4,820,523 | 4/1989 | Shtohryn et al. | 424/470 |
| 4,828,820 | 5/1989 | Glass et al. | 424/440 |
| 4,879,108 | 11/1989 | Yang et al. | 424/440 |
| 4,894,234 | 1/1990 | Sharma et al. | 424/440 |
| 4,937,076 | 6/1990 | Lapidus | 424/41 |
| 4,975,270 | 12/1990 | Kehoe | 424/442 |
| 4,988,683 | 1/1991 | Corbiere | 514/165 |

FOREIGN PATENT DOCUMENTS

| | | |
|---|---|---|
| 893729 | 1/1983 | Belgium . |
| 0151344 | 8/1985 | European Pat. Off. . |
| 0236271 | 9/1987 | European Pat. Off. . |
| 0253040 | 1/1988 | European Pat. Off. . |
| 8806449 | 9/1988 | WIPO . |

*Primary Examiner*—D. Gabrielle Brouillette
*Attorney, Agent, or Firm*—Sprung Kramer Schaefer & Briscoe

[57] ABSTRACT

The invention relates to stable, pharmaceutically usable chewing gum formulations which contain acetylsalicylic acid (ASA) as the active compound, and to a process for their preparation.

5 Claims, No Drawings

PHARMACEUTICAL CHEWING GUM CONTAINING ACETYLSALICYLIC ACID

This application is a continuation of application Ser. No. 824,425, filed Jan. 23, 1992, now abandoned.

The invention relates to stable, pharmaceutically usable chewing gum formulations which contain acetylsalicylic acid (ASA) as the active compound, and to a process for their preparation.

Acetylsalicylic acid is a medicament which has been known for a long time and has antipyretic, anti-inflammatory and analgesic properties. Acetylsalicylic acid is employed for relatively long periods of time and in high doses for the treatment of rheumatic diseases. Acetylsalicylic acid has an inhibiting action on platelet aggregation, the acetylation of platelet cyclooxygenase presumably playing an important role. This property of the substance is utilised in its use for the prophylaxis and treatment of thromboses and in the field of other cardiovascular diseases. Relatively low doses are effective in this indication.

Acetylsalicylic acid is absorbed relatively slowly. On oral administration, the blood level maximum is reached only after about 2 hours. The substance undergoes a metabolic change after this administration, in the course of which acetic acid is split off. The first step of this reaction is effected by the esterases of the mucosa, and the subsequent reaction by the esterases in the liver, plasma and erythrocytes. Because of the associated high rate of metabolisation, the slow absorption is particularly undesirable in the indication of platelet aggregation inhibition, since the unchanged acetylsalicylic acid molecule is the active form here.

Like other organic acids, acetylsalicylic acid has a locally irritating and tissue-damaging action. As a result of damage to the gastric mucous membrane, micro-haemorrhages occur not infrequently when this compound is used. Dangerous haemorrhages may occur if ulcers are present in the gastrointestinal region. The risk of damage to the gastric mucous membrane increases in this context as the dose administered increases.

For the abovementioned reasons, it is appropriate to seek pharmaceutical presentation forms for acetylsalicylic acid which on the one hand ensure rapid absorption and on the other hand have good gastric tolerance.

One possibility of solving the problems mentioned is to use effervescent formulations containing acetylsalicylic acid. However, these have the following disadvantages:

A glass of clean water and at least 2 to 3 minutes' time are needed to take them. They are therefore not suitable, for example, for travelling.

They usually have a high sodium content.

Their preparation and packaging in moisture-proof packing agents must be carried out under a particularly low atmospheric humidity, and are therefore involved and expensive.

Effervescent formulations are high-cost products.

Chewable compositions (chewing gum, bubble gum, stick gum) were already described in the last century, and chewing gums and chewable tablets with a medicinal use have also been known for a very long time. The first chewing gum formulation containing acetylsalicylic acid was brought onto the market in the USA in 1924.

Chewing gum formulations which contain acetylsalicylic acid are also mentioned in the literature. For example, U.S. Pat. No. 2,465,233 describes a chewing gum for the treatment of kinetoses which contains a combination of scopolamine hydrobromide and acetylsalicylic acid. EP 0,151,344 describes a chewing gum formulation which is suitable for the preparation of chewing gum tablets and can contain pharmaceutical active compounds, ASA being mentioned. EP 0,253,040 describes a process for the preparation of a chewing gum sweet, medicaments of the acetylsalicylic acid type being described as possible components.

All the examples mentioned have the common serious disadvantage that when the formulation is chewed in the mouth, a solution of low pH is formed. This solution leads to irritation of the oral mucous membrane and damage to the tooth enamel, and the last point in particular is currently regarded very critically from the point of view of caries prevention. FR 87/02,939 offers a solution to this problem, in which the lysine salt of acetylsalicylic acid is employed here as the active compound in a buccal medicament form. However, no medicament forms which have an adequate chemical stability can be prepared in the manner described in that publication. The resistance of acetylsalicylic acid to hydrolysis decreases as the pH increases. The stability optimum is in the pH range of 2 to 3 (compare DAB 9, page 769, commentary). It is also expressly pointed out there that ASA is incompatible with alkaline substances. This means that all salts, including the lysine salt, have a lower stability than the free acid. Since the preparation of stable formulations of the free acid is already associated with major difficulties, even less success is to be expected when salts of acetylsalicylic acid are used.

It has now been found, against expectations, that with the composition according to the invention and the use of a specific preparation process it is possible to prepare stable, pharmaceutically usable ASA-containing chewing gum formulations which eliminate all the abovementioned disadvantages and are suitable for administration of all the customary doses of ASA. Astonishingly, it has been possible to combine the advantages of the buccal medicament forms already known, that is to say the good mucous membrane and mucosa tolerance of the chewing formulation containing ASA on the one hand and the good stability of the medicament forms containing the free acid on the other hand by the formulation according to the invention, without the particular disadvantages having to be the price.

The invention relates to a stable chewing gum formulation which is tolerated by the mucous membrane and contains acetylsalicylic acid as one component and a basic substance suitable for salt formation as the second component in a spatially separated form. During the chewing operation, the two components are dissolved out of the matrix and react immediately in the form of an acid-base reaction to give the particular readily soluble salt of acetylsalicylic acid. During storage of the formulation, the ASA is present as the free acid and therefore has a correspondingly high chemical stability, and the salt of ASA or a solution of this salt, which has a considerably improved mucous membrane tolerance compared with the free acid and attacks the tooth enamel less, is formed during the chewing operation.

The chewing gum formulation according to the invention preferably has the following composition:

| | |
|---|---|
| Acetylsalicylic acid | 2–30 parts by weight corresponding to 30–1500 mg |
| Basic buffer substances | corresponding to 0.1–17 meq* buffer capacity |
| Chewing gum base | 15–50 parts by weight |
| Plasticiser | 0–30 parts by weight |
| Sugar and/or sugar substitutes | 0–55 parts by weight |

-continued

| | |
|---|---|
| Sweetener | 0–2 parts by weight |
| Aroma substances | 0–5 parts by weight |
| Fillers | 0–30 parts by weight |
| if appropriate other components such as waxes, emulsifiers; stabilisers | 0–20 parts by weight |
| if appropriate water-soluble polymer | 0–30 parts by weight |

*corresponding to USP XXII

Chewing gum bases as a rule consist of two main components which are needed to achieve the desired chewing gum properties. An elastomer component A represents the water-insoluble content which forms the volume, and a resinous, similarly water-insoluble component B is responsible for the constant chewability of the material. Both the elastomer component A and the resinous addition B can be of natural or synthetic origin. A combination of naturally occurring and synthetic material is also possible.

Possible elastomer components A are all the elastomers which are known to the expert and are physiologically tolerated. These can be, for example: natural rubber, such as chicle, polyvinyl acetates, isobutylene-isoprene copolymers, styrene-butadiene copolymers, polyiso-butylene, guttapercha, crown rubber, polyisoprene, polyethylene, naturally occurring polyterpenes and mixtures of these.

The resin components B usually used are, for example, Arkon P, polyvinyl esters of suitable molecular weight (for example polyvinyl acetate of molecular weight 20,000), copolymers of vinyl esters and vinyl ethers, polyethylene-vinyl acetate copolymers and natural resins, such as, for example, dammar and guaiacum.

Commercially available chewing gum bases can also be used according to the present invention as matrices for the chewing gum composition. Basic buffer components which can be employed are alkaline earth metal carbonates, preferably calcium carbonate; however, it is also possible to use calcium hydroxide, magnesium hydroxide, light magnesium carbonate, heavy magnesium carbonate or magnesium oxide. Other possible basic components are, for example, tris-(hydroxymethyl)-aminomethane, alkali metal phosphates or alkaline earth metal phosphates and basic amino acids. The amount of basic component is chosen according to the invention so that, together with the amount of acetylsalicylic acid employed, a buffer capacity of between 5 and 15 mEq results.

If appropriate, other constituents known to the expert for plasticising and texturising, for example fats and waxes, emulsifying, for example lecithin, filling, for example talc, aromatising and/or for establishing other required properties can be incorporated into the chewing gum base. The chewing gums can be sugar-free or can contain sugar. Compounds which are suitable for sweetening are sugars and sugar substitutes, such as mono- and disaccharides, hydrolysates of high molecular weight carbohydrates and sugar-alcohols. All or some of the amount of these substances can also be replaced by sweeteners, such as, for example, saccharin, cyclamate or aspartame.

The chewing gum base consisting of components A and B, including the additives mentioned, is called the chewing gum matrix below.

The constituents of a chewing gum formulation which are usually automatically necessary are the water-insoluble inert chewing gum base and the water-soluble content which is gradually dissolved out of the chewing gum matrix by the saliva during chewing. The formation of a (salt) solution of ASA from the formulation according to the invention in the saliva in the mouth is desirable for the following reasons: in this way acetylsalicylic acid enters the stomach only in dissolved form, so that the formation of areas of high active compound concentrations in the stomach is avoided. This achieves an optimum gastric tolerance in the region of that of an effervescent tablet.

Significant amounts of the substance can already be absorbed from the saliva solution via the oral mucous membrane regardless of the residence time in the mouth. Acetylsalicylic acid in this way passes rapidly and in non-metabolised form into the circulation and can display its action there rapidly and effectively.

The abovementioned problem that the active compound solution formed in the mouth can cause damage to the oral mucous membrane and in particular the teeth is solved according to the invention by addition of a basic component which converts the chewing gum into a buffered formulation. Scanning electron microscopy examinations of extracted human teeth show that the damage to tooth enamel caused by solutions of acetylsalicylic acid can be reduced drastically and brought within the range of a placebo solution by suitable buffering. The risk described for some chewing tablets known to date that, for example, pieces of tablet which have remained in the cheek pouch overnight can cause severe inflammations of the oral mucous membrane also does not exist with the new chewing gum formulation, since acetylsalicylic acid emerges from the chewing gum matrix only in dissolved and therefore readily mobile form and at the same time is buffered. Local toxic concentrations are therefore not to be feared with the form according to the invention.

To prevent the known hydrolytic decomposition of acetylsalicylic acid, and in particular of its salts, which is accelerated considerably by heat, moisture and alkaline substances, the following measures are used individually or in combination in the preparation, according to the invention, of the formulation:

1. the water content of the product is kept as low as possible,
2. the exposure to heat during the preparation is kept low and
3. the acetylsalicylic acid is separated spatially from the basic component.

Re 1.:

A chewing gum matrix having a water content of not more than 2%, preferably up to 1%, in particular up to 0.3% (per cent by weight) is used for the chewing gum formulation according to the invention. To achieve the desired low water content, in particular the chewing gum bases, the plasticisers and the sweeteners should be of low water content and only slightly hygroscopic.

Re 2.:

Temperatures of more than 90° C. are often used in the preparation of chewing gum. In contrast, a maximum temperature of 85° C. is not exceeded in the preparation according to the invention of the chewing gum described. The ideal process temperature for the preparation is 40° C. and the preferred temperature range according to the invention is between 20 and 85° C., in particular between 30 and 60° C.

Re 3.:

a) Direct contact between the active compound component ASA and the basic component in the formulation is prevented by the two components being incorporated independently of one another and individually into a relatively large amount of chewing gum matrix, so that most of the acid particles are embedded individually in the matrix and are separated from their adjacent basic particles by the chewing gum base or the other additives and vice versa. As a result of the water content of the matrix being low according to the invention, solution processes and diffusion via the liquid phase are not to be expected.

b) If it is necessary, for example at high concentrations of acetylsalicylic acid and basic buffer substance, to realise a more complete spatial separation of the two components, a preferred embodiment is to additionally coat one of the two substances or even both substances with a protective separating layer. The separating layer consists, for example, of a water-soluble polymer film which is applied to the substance to be protected. Hydroxypropylmethylcellulose (HPMC) is particularly preferably used as the water-soluble polymer, but it is also possible to use other cellulose derivatives or water-soluble polymers, such as starch derivatives, polyacrylates, alginates and the like. The polymer is used in an amount by weight of 1 to 100% of the core weight of the substance to be coated, such as ASA or base. The coating weight is preferably between 5 and 30% of the core weight, the amount to be particularly preferably applied depending on the particle size of the core particles.

The preferred process for application of the protective separating layer is spraying of the polymer from an aqueous solution onto the material to be coated.

The basic component is preferably coated or granulated with the water-soluble polymer, since this avoids the risk that the acetylsalicylic acid will be decomposed by hydrolysis during the coating process.

c) Another possibility of spatial separation of the two components comprises first incorporating the basic component into one half of the chewing gum base. ASA is then incorporated into the other half of the corresponding chewing gum base. Contact between the two compounds is largely avoided in this preparation process, since there is merely a reduced possibility of contact during subsequent common mixing and shaping of the two "prebatches". Most of the powder particles in these mixtures are also embedded in the chewing composition in isolated form. This process, which is comparable to a), thus represents a further improvement on the basis of the modified mixing procedure.

d) A significantly improved spatial separation can also be achieved by bringing the "prebatches" described under c) together in a final shaping operation without the compositions being mixed directly during this operation. Processes which are suitable for this are, inter alia, coextrusion via multilayer dies (adapter and in particular die coextrusion to give multilayer films/sheets) and, for example, calendering processes for the production of multilayer systems. All the apparatuses suitable in the rubber and foodstuffs industry can be used for this purpose.

The particular advantage of such a preparation process lies in the fact that the base compositions described under a), one of which contains the basic component and the other the ASA, come into contact merely via the "interfaces" of the coextrudates or films. This process is therefore particularly suitable for formulations with a high active compound concentration, since mixing of the base compositions during preparation is excluded. Each individual particle is thus present in the matrix in isolated form, which ensures a high storage stability.

e) Another possibility for spatial separation of the two individual components comprises modification of the operation, described under c), of separate mixing of the two components into a base chewing composition such that one component is first incorporated into the chewing gum base in the customary manner. The second component is then incorporated into a physiologically acceptable polymer composition which is only partly compatible with the chewing gum base. Subsequent joint compounding of the two base compositions in customary mixing units, such as, for example, kneaders, mills or extruders, leads to generally known morphological structures on the basis of the partial compatibilities existing between the two polymer systems. In these structures, for example, one component is present as a dispersion in the other. Such a structure is in principle related to that described under d), since here also contact is possible only via "interfaces" (matrix and disperse components). However, these structures offer the advantage that there is already a tight spatial closeness between the two components here over the entire homogeneously mixed blend, without contact between the two components being possible. The desired salt formation during a subsequent chewing operation can thus take place much more rapidly.

The chewing gum compositions are obtained by bringing the chewing gum base, if appropriate the other additives, the acetylsalicylic acid and the (optionally coated) basic component into contact in a mixing unit. Solid particles having a particle size of less than 50 $\mu$m are particularly preferred. Although higher particle sizes can be incorporated without problems, a modified chewing sensation is to be expected.

The chewing gum compositions according to the invention can be prepared by various processes. The process can be carried out discontinuously or continuously. Customary processes are, for example, preparation on mixing mills, kneaders and extruders. All the customary apparatuses and methods for the preparation of chewing gum are generally suitable for the preparation of the chewing gum compositions according to the invention. Processing of the chewing gum compositions to strips, tablets or balls and packaging thereof are also carried out by customary methods and can be undertaken on any known machine suitable for shaping and packaging chewing gum.

The chewing gum compositions according to the invention are preferably prepared by rolling the chewing gum base on a heatable roll at a roll speed of about 10–40 revolutions per minute in a temperature range from 20 to 85° C. for some minutes, subsequently adding acetylsalicylic acid, flavouring substances, plasticisers and if appropriate other auxiliaries and if appropriate then adding the basic buffer substance directly or incorporating the basic buffer substance in a portion of the chewing gum base on a correspondingly heated roll in a separate process step, the compounding time in each case being between 3 and 15 minutes, subsequently removing the chewing gum composition from the roll and, after cooling to room temperature, further processing the composition to finished chewing gum formulations in the customary manner.

At no point in time should the roll temperature exceed 85° C., preferably 60° C. If necessary, the roll temperature is reduced by cooling if heat of friction which is too high occurs.

The chewing gum formulations according to the invention prepared in this way offer the advantage of rapid absorption of the acetylsalicylic acid which is already present in dissolved form in the mouth, the advantage of a good tolerance in the mouth and in the stomach due to salt formation and buffering of the resulting solution during the chewing operation, the advantage of a high bioavailability due to the low metabolisation on buccal absorption, and the advantage of a high storage stability, since the acetylsalicylic acid is present as the free acid during storage. The disadvantages of the ASA-containing medicament forms known to date, each of which offer only one or not more than two of the advantages mentioned, are avoided by the formulation according to the invention.

EMBODIMENT EXAMPLES

Example 1

(variant 3a)

| Cafosa Gum Base TAB-3-T | 32 | g |
|---|---|---|
| Sugar | 44 | g |
| Cafosa Plasticiser 1001-01 | 3 | g |
| Optamint peppermint (H&R) | 4.2 | g |
| Citric acid | 0.8 | g |
| ASA | 10 | g |
| Calcium carbonate | 6 | g |

32 g of a chewing gum base (Cafosa Gum Base TAB-3-T) are introduced onto a roll heated at 50° C. and rolled for 3 minutes. 44 g of sugar are then added. After about 3 minutes, a homogeneous mass is obtained, into which the other components are incorporated individually in succession. The peppermint flavouring substance (4.2 g) and the citric acid (0.8 g) are first added. 3 g of Cafosa Plasticiser 1001-01, 6 g of basic buffer substance (calcium carbonate) and 10 g of ASA are then incorporated. After a total milling time of 10.5 minutes, the chewing gum composition is removed from the roll. After cooling to room temperature, the finished material can be further processed to any desired shape.

Example 2

(variant 3b)

| Cafosa Gum Base Dorada Plus-T | 32 | g |
|---|---|---|
| Sorbitol powder | 22.8 | g |
| Xylitol powder | 5 | g |
| Optamint peppermint (H&R) | 4.5 | g |
| Cafosa Plasticiser 1001-01 | 2 | g |
| Aspartame | 0.5 | g |
| ASA | 20 | g |
| Calcium carbonate | 12 | g |
| HPMC | 1.2 | g |

32 g of Gum Base Dorada Plus-T are introduced onto a roll heated to 60° C. and rolled for 3 minutes. 22.8 g of sorbitol powder and 5 g of xylitol powder are then added to this chewing gum matrix. After a further rolling time of 3 minutes, 4.5 g of Optamint peppermint flavouring substance, 0.5 g of aspartame and 2 g of Cafosa Plasticiser are added. Finally, 20 g of ASA and 13.2 g of calcium carbonate/HPMC are incorporated. For this, 12 g of calcium carbonate are treated by spraying on a separating layer of 1.2 g of HPMC (hydroxypropyl-methylcellulose) in a preceding operation for the purpose of complete spatial separation from the acetylsalicylic acid.

Example 3

| Cafosa Gum Base TAB-3-T | 30 | g |
|---|---|---|
| Sorbitol powder | 19.5 | g |
| Na cyclamate/Saccharin Na | 0.5 | g |
| Ascorbic acid | 1 | g |
| ASA | 30 | g |
| Calcium carbonate | 18 | g |
| HPMC | 1 | g |

This chewing gum composition is prepared analogously to Example 2.

Example 4

(variant 3c)

| Cafosa Gum Base Dorada Plus-T | 30 | g |
|---|---|---|
| Sugar | 15 | g |
| Sorbitol powder | 29 | g |
| Ascorbic acid | 1 | g |
| ASA | 15 | g |
| Calcium carbonate | 10 | g |

To prepare this chewing gum composition, 30 g of Cafosa Gum Base Dorada Plus-T are rolled on a laboratory roll at 45° C. for 3 minutes. 15 g of sugar, 29 g of sorbitol powder and 1 g of ascorbic acid are then added. The mixture is rolled for a further 4 minutes until a homogeneous material is obtained. The chewing gum composition is then divided into two halves (prebatches 1 and 2). 15 g of ASA are incorporated into one half (prebatch 1) over a milling time of 2.5 minutes, and 10 g of calcium carbonate, as the basic buffer substance, are incorporated into the other half (prebatch 2). As a result, most of the ASA and base particles are present in these mixtures embedded in the chewing gum composition in isolated form. The preparation of prebatches 1 and 2 is followed by a very short joint mixing operation and subsequent shaping.

Example 5

(variant 3d)

| Cafosa Gum Base TAB-3-T | 28 | g |
|---|---|---|
| Sorbitol powder | 39.5 | g |
| Na cyclamate | 0.5 | g |
| ASA | 20 | g |
| Calcium carbonate | 12 | g |

Two prebatches are first prepared according to Example 4, one of which contains the total amount of ASA corresponding to the recipe and the other prebatch containing the total amount of calcium carbonate corresponding to the recipe. The two prebatches are passed to a unit for preparation of multilayer systems and are brought together such that there is no direct mixing of the compositions here. For this purpose, the prebatches are fed to two separate feeding devices of a coextruder and are then coextruded to strands at a die temperature of not more than 85° C.

Example 6

| Chewing gum base 1 | 13 | g |
|---|---|---|
| Chewing gum base 2 | 14 | g |
| Cafosa Plasticiser 1001-01 | 3 | g |
| Sugar | 15 | g |
| Sorbitol powder | 29 | g |
| Ascorbic acid | 1 | g |
| ASA | 15 | g |
| Calcium carbonate | 10 | g |

To prepare this chewing gum composition, two different chewing gum bases which are only partly compatible with one another are used. All the polymers which are suitable for preparation of chewing gum bases (compare page 6) and have a mutual partial compatibility can in principle be used here.

To prepare this chewing gum composition according to the invention, 13 g of a chewing gum base 1 which contains natural rubber are rolled on a laboratory roll at 85° C. for 3 minutes. 7.5 g of sugar, 14.5 g of sorbitol powder, 1.5 g of Cafosa Plasticiser, 15 g of ASA and 1 g of ascorbic acid are then added. The mixture is rolled for a further 4 minutes until a homogeneous material is obtained (prebatch 1). Another prebatch consisting of 14 g of the chewing gum base 2 containing styrobutadiene copolymer, 7.5 g of sugar, 14.5 g of sorbitol powder, 1.5 g of Cafosa Plasticiser and 10 g of calcium carbonate is then prepared by the same procedure (prebatch 2). Final joint compounding of the two prebatches in a mixing kneader leads to generally known morphological structures, on the basis of the partial compatibility which exists between the two chewing gum bases, in which one chewing gum base is present as a dispersion in the other.

We claim:

1. An acetylsalicyclic acid-salt releasing chewing gum comprising acetylsalicylic acid, and a basic substance capable of reacting with said acetylsalicylic acid to form an acetylsalicylic acid salt, said gum containing not more than about 2% of water and said acetylsalicylic acid and said basic substance being bound in said chewing gum apart from each other sufficiently to prevent them from reacting with each other until said chewing gum is chewed, which gum when chewed in the presence of saliva brings said acetylsalicylic acid into contact with said basic substance so that they react to form said acetylsalicylic acid salt which is then rapidly released to the saliva, said basic substance being selected from the group consisting of an alkaline earth metal carbonate, calcium hydroxide, magnesium hydroxide, light magnesium carbonate, heavy magnesium carbonate or magnesium oxide, tris-(hydroxymethyl)-aminomethane, alkali metal phosphates or alkaline earth metal phosphates and basic amino acids, the amount of basic substance being such that together with the amount of acetylsalicylic acid employed there results a buffer capacity of between 5 and 15 mEg.

2. Chewing gum formulation according to claim 1, having the following composition:

| | |
|---|---|
| Acetylsalicylic acid | 2–30 parts by weight corresponding to 30–1500 mg |
| Basic buffer substances | corresponding to 0.1–17 meq buffer capacity |
| Chewing gum base | 15–50 parts by weight |
| Plasticiser | 0–30 parts by weight |
| Sugar and/or sugar substitutes | 0–55 parts by weight |
| Sweetener | 0–2 parts by weight |
| Aroma substances | 0–5 parts by weight |
| Fillers | 0–30 parts by weight |
| waxes, emulsifiers, stabilisers | 0–20 parts by weight |
| water-soluble polymer | 0–30 parts by weight. |

3. Chewing gum formulation according to claim 1, per 100 parts by weight consisting essentially of

| | |
|---|---|
| Acetylsalicylic acid | 2–30 parts by weight corresponding to 30–1500 mg |
| Basic buffer substances | corresponding to 0.1–17 meq buffer capacity |
| Chewing gum base | 15–50 parts by weight |
| Plasticiser | 0–30 parts by weight |
| Sugar and/or sugar substitutes | 0–55 parts by weight |
| Sweetener | 0–2 parts by weight |
| Aroma substances | 0–5 parts by weight |
| Fillers | 0–30 parts by weight |
| Waxes, emulsifiers, stabilizers | 0–20 parts by weight |
| Water-soluble polymer | 0–30 parts by weight |
| Water | 0–2 parts by weight. |

4. Chewing gum formulation according to claim 1, characterized in that the spatial separation between the components acetylsalicylic acid and the basic buffer substance is ensured by one or more of the following measures:

a) the two components are incorporated independently of one another and individually into the chewing gum matrix, b) one or both components are coated with a protective separating layer of a water-soluble polymer film, c) the two components are in each case incorporated independently of one another into the chewing gum composition and these compositions are mixed just before shaping or coextruded via multiple dies, or d) the two components are in each case incorporated independently of one another into different chewing gum bases or polymer compositions which are only partly compatible with one another, a two-phase system being formed during joint compounding and shaping of the two matrices.

5. Process for the preparation of chewing gum formulations according to claim 1, characterized in that the acetylsalicylic acid, the chewing gum base, and additives and the basic component, which is optionally coated and/or worked into a chewing gum base which is optionally partly compatible, are converted into application form continuously or discontinuously in a mixing unit at temperatures between 20 and 85° C.

* * * * *